US005670879A

United States Patent [19]
Zombo et al.

[11] Patent Number: 5,670,879
[45] Date of Patent: Sep. 23, 1997

[54] NONDESTRUCTIVE INSPECTION DEVICE AND METHOD FOR MONITORING DEFECTS INSIDE A TURBINE ENGINE

[75] Inventors: Paul J. Zombo, Cocoa, Fla.; Paul Guenther, Murrysville, Pa.; Charles C. Moore, Hibbs, Pa.; Michael J. Metala, Murrysville, Pa.

[73] Assignee: Westinghouse Electric Corporation, Pittsburgh, Pa.

[21] Appl. No.: 165,289

[22] Filed: Dec. 13, 1993

[51] Int. Cl.$^6$ .......................... G01N 27/90; G01N 27/82; G01M 1/22
[52] U.S. Cl. .................. 324/227; 324/262; 73/660
[58] Field of Search ........................ 324/237, 238, 324/240, 241, 242, 243, 226, 227, 207.25, 174, 262; 73/660, 661

[56] References Cited

U.S. PATENT DOCUMENTS

| | | | |
|---|---|---|---|
| 4,139,822 | 2/1979 | Urich et al. | 324/219 |
| 4,380,172 | 4/1983 | Imam et al. | 73/660 |
| 4,507,608 | 3/1985 | Flach et al. | 324/237 |
| 4,646,010 | 2/1987 | Bystrom et al. | 324/207.22 |
| 4,685,335 | 8/1987 | Sato et al. | 73/660 |
| 4,741,203 | 5/1988 | Willaman et al. | 73/116 |
| 4,763,274 | 8/1988 | Junker et al. | 324/238 |
| 4,866,381 | 9/1989 | Tatsuhiko | 324/207.25 |
| 4,902,971 | 2/1990 | Guzik et al. | 324/212 |
| 4,955,269 | 9/1990 | Kendig et al. | 73/660 |
| 5,041,785 | 8/1991 | Bogaerts et al. | 324/207.24 |
| 5,140,264 | 8/1992 | Metala et al. | 324/227 |
| 5,287,735 | 2/1994 | Klauber et al. | 73/660 |
| 5,329,230 | 7/1994 | Viertl et al. | 324/238 |

*Primary Examiner*—Sandra L. O'Shea
*Assistant Examiner*—Roger C. Phillips

[57] ABSTRACT

A nondestructive inspection device and a method of monitoring a defective condition in a rotating member of a combustion turbine engine using a nondestructive inspection device is presented. The nondestructive inspection device includes a sensor for monitoring the rotating member and a holder assembly for positioning the sensor near the rotating member without disassembling the combustion turbine engine. The holder assembly is capable of interchangeably positioning either an ultrasound transducer or an eddy current sensor. Signals indicative of the monitored condition are recorded and compared to a signal representation generated from a reference standard having a known defect so that a defective condition can be ascertained. The location of a defective condition is ascertained by using a magnetic belt having a plurality of magnets wrapped around the rotating member and an additional sensor to detect the magnets as they rotate. A signal indicative of the detected magnets is recorded along with the signal indicative of the monitored condition so that the angular position of the rotating member can be correlated with a detected defect.

16 Claims, 3 Drawing Sheets

NONDESTRUCTIVE INSPECTION DEVICE AND METHOD FOR MONITORING DEFECTS INSIDE A TURBINE ENGINE

FIELD OF THE INVENTION

The present invention is directed to a nondestructive inspection device and method for monitoring a defective condition of a rotating member. More particularly, the present invention is directed to a nondestructive inspection device and method for identifying the formation of a crack in the air separator of a combustion turbine engine.

BACKGROUND OF THE INVENTION

Large combustion turbines are very similar to turbine engines on modern jet aircraft. Combustion turbines manufactured for the electric utility industry are large in size and generate as much as 200 MW of power. As a result, the operational environment within a combustion turbine engine is high in temperature, pressure, and vibration. Therefore, the combustion turbine components are susceptible to surface cracking or fracturing and other forms of degradation.

FIG. 1 is a cross-sectional view of a 501F, 140 MW combustion turbine. Of particular interest is the air separator 10 which maintains an air seal separating compressed air for the burning cycle from cooling air for the turbine blades 22. As shown in FIG. 1, the air separator 10 meets with the combustion turbine discs 20 as shown generally at 25. Therefore, one face of the air separator 10 is "hidden" where it meets the first of the combustion turbine discs 20 which is referred to as the row 1 disc 15. Recently, the formation of a crack in the air separator 10 has been identified as a cause of failure of combustion turbine engines. Once the combustion turbine is in operation cracks can develop on the hidden face of the air separator 10. FIG. 2A is a enlarged view of the portion of the combustion turbine 25 where the air separator 10 meets with the first of the combustion turbine discs 20.

It has been determined that the formation of a crack begins at the air separator/row 1 disc contact interface 30. FIG. 2B is a three dimensional representation of the portion of the air separator 10 shown in FIG. 2A having a crack 32 forming on the surface of the air separator 10. FIG. 2C is a top surface view of the same portion of the air separator 10 showing the crack 32 progressing from the contact interface 30 away from the row 1 disc 15.

When the combustion turbine is assembled the air separator 10 and more particularly the air separator/row 1 disc contact interface 30 are completely hidden from view and inaccessible for normal inspection. Therefore the combustion turbine must be disassembled if the air separator 10 or the contact interface 30 are to be inspected. Turbine disassembly is very time consuming and expensive. As a result, there is a need to inspect the air separator ring 10 without disassembly.

SUMMARY OF THE INVENTION

It is therefore an object of the present invention to provide a nondestructive inspection device and a method for inspecting a rotating member for a defective condition that does not require disassembly of machinery such as a combustion turbine engine.

A nondestructive inspection device according to one embodiment of the present invention fulfills this objective by providing an inspection sensor which is positioned near the surface of the rotating member by a holder assembly. The inspection sensor monitors the rotating member for a defective condition and outputs a signal related thereto. An angular position identification means generates a signal indicating the angular position of the rotating member as it rotates. A recorder is also provided to record the signals related to the condition being monitored and the angular position of the rotating member. Based on the recorded signal, a skilled operator could identify a defective condition and its location in the rotating member.

In a preferred embodiment, the inspection sensor is either an eddy current sensor or an ultrasound transducer, and the holder assembly is configured to interchangeably position either of these sensors. In another preferred embodiment, the recorder is either a strip chart recorder or a data processor having a memory and a display. In still another preferred embodiment, the angular position identification means provides a magnetic belt having a plurality of magnets which is wrapped around the rotating member. An additional sensor, such as an eddy current sensor, detects the magnets as they rotate with the rotating member. The additional sensor provides a signal to the recorder indicating each magnet it detects as they rotate.

The holder assembly according to the present invention comprises an axial member such as a lead screw. A locking device and an attachment apparatus are connected to the axial member. The locking device clamps the holder assembly in place and the attachment apparatus connects either type of sensor to the axial member. The axial member, can be adjustably extended and its vertical position can be adjusted using an axial adjustment means and seating adjustment means, respectively, in a preferred embodiment of the invention. If an ultrasound transducer is used as the sensor, further adjustment means are provided for adjusting the angular skew of the ultrasound transducer and the size of the couplant gap to optimize the transmission of the ultrasound.

A method is also provided by the present invention in which a characteristic of a rotating member is sensed by a nondestructive inspection device. A signal indicative of the sensed characteristic is then generated and recorded. That signal is then compared to a known signal representation to identify the existence of a defective condition in the rotating member. The known signal representation is preferably generated by calibrating the inspection device using a reference standard having a known defect. A signal is generated from the calibration step and is then recorded. In a further preferred embodiment the angular position of the defect, if one exists, is also determined by monitoring the rotation of the rotating member.

BRIEF DESCRIPTION OF THE DRAWINGS

The present invention will be better understood, and its numerous objects and advantages will become apparent by reference to the following detailed description of the invention when taken in conjunction with the following drawings, in which.

DETAILED DESCRIPTION OF THE INVENTION

Figure 1:
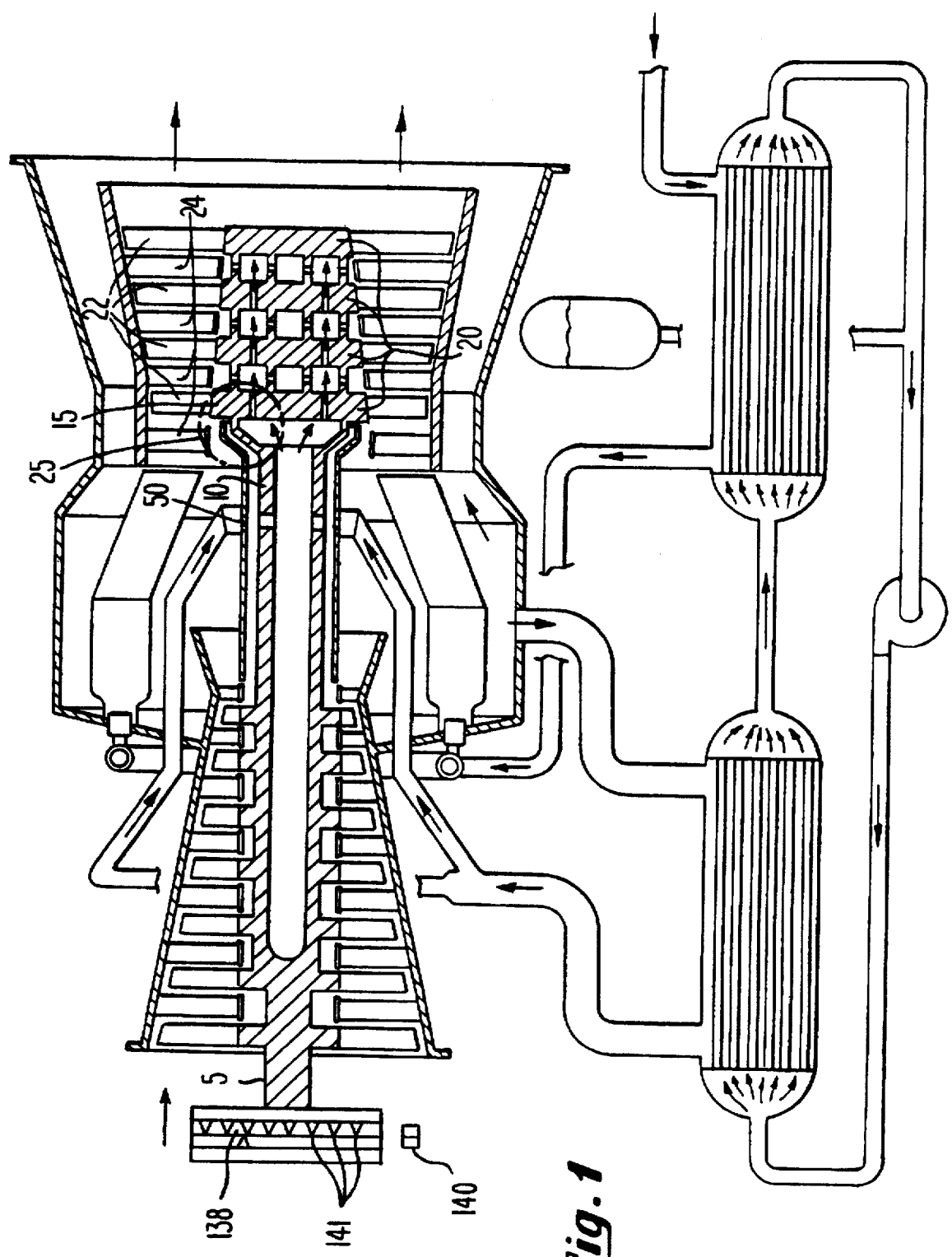
FIG. 1 is a cross-sectional view of a combustion turbine engine.
Figure 2A:
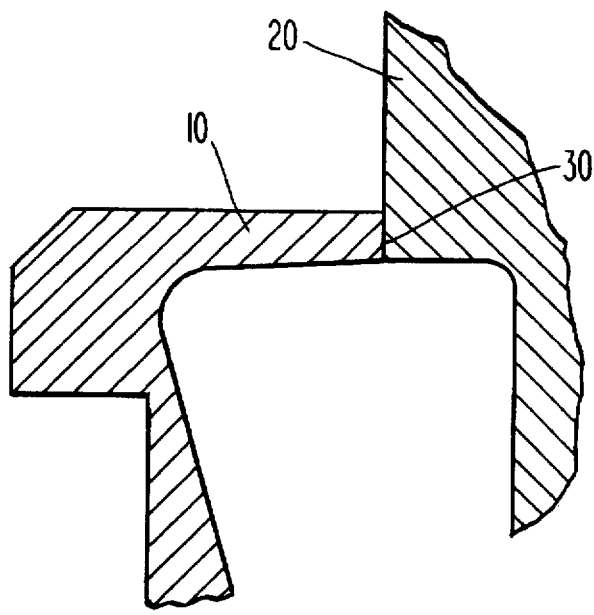
FIG. 2A is enlarged cross-sectional view of the air separator and combustion turbine disc interface.
Figure 2B:
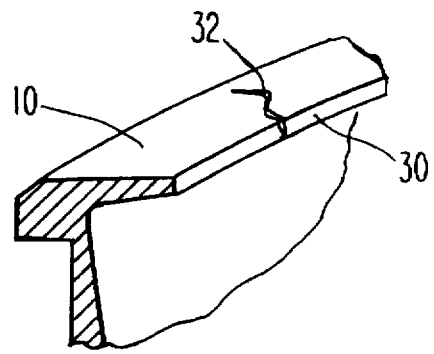
FIG. 2B is a three dimensional representation of the air separator having a crack formation.
Figure 2C:
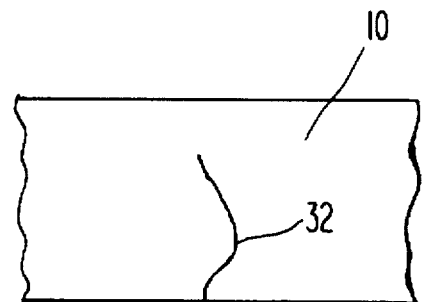
FIG. 2C is a top surface view of the air separator showing the progression of a crack in the air separator.

Like reference numerals refer to like elements in the figures. Although it should be understood that the nondestructive inspection device of the present invention could be used for a number of different applications and for monitoring numerous conditions or characteristics of a rotating member, it will be described herein in connection with its use in monitoring crack formation in a combustion turbine air separator.

Figure 3:
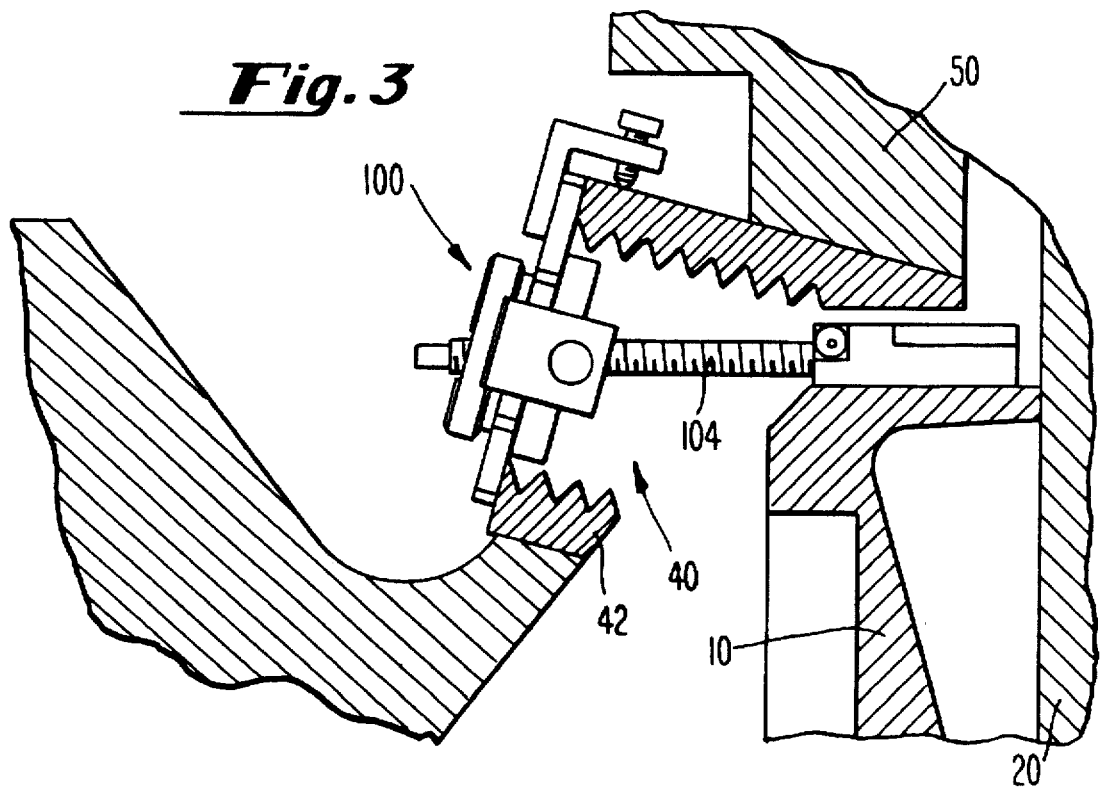
FIG. 3 is a cross-sectional view of the inspection device according to the present invention positioned within an access port in a combustion turbine engine.

A cross sectional view of a preferred embodiment of the inspection device within the combustion turbine for monitoring the air separator is shown in FIG. 3. An access port 40 is formed in the torque tube housing 50. The inspection device shown generally at 100 may be inserted through the opening of the access port 40 so that it extends towards the combustion turbine discs 20 over the surface of the air separator 10.

Figure 4:
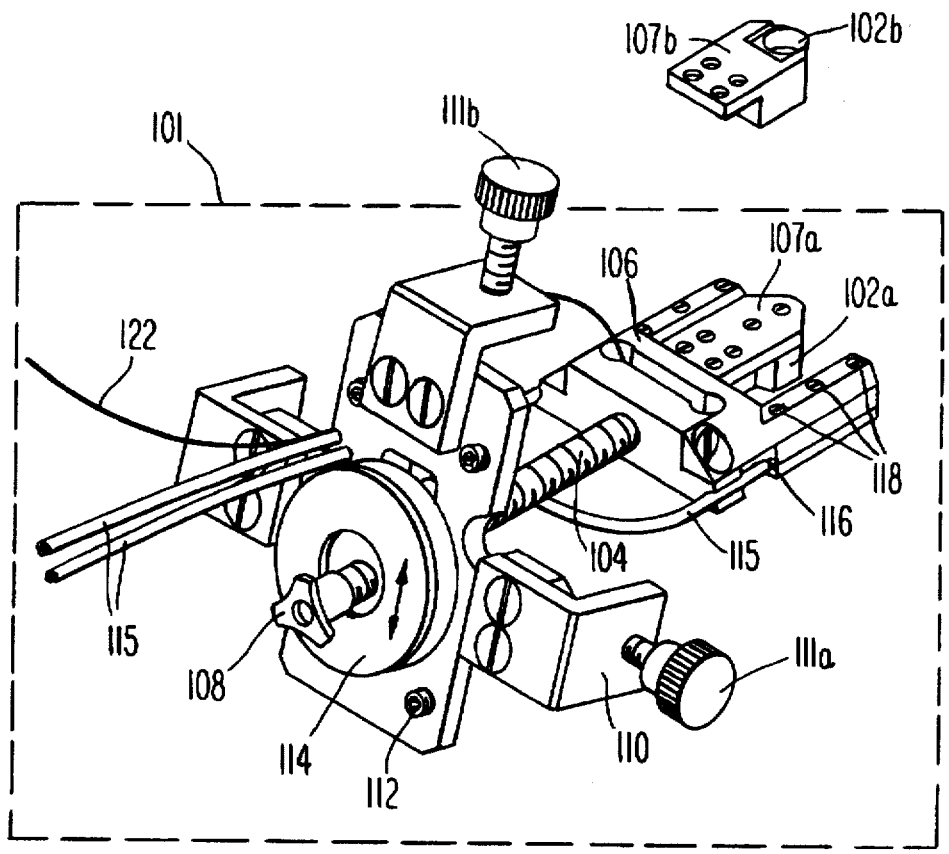
FIG. 4 is a detailed diagram of the inspection device according to a preferred embodiment of the present invention.

FIG. 4 is a detailed diagram of a nondestructive inspection device according to a preferred embodiment of the present invention. The inspection device preferably comprises two primary elements, the holder assembly 101 and a sensor 102a or 102b. The sensor 102a or 102b is preferably attached to the holder assembly 101 at one end. In preferred embodiments the sensor may be either an ultrasound transducer 102a or an eddy current sensor 102b. It should be understood that an ultrasound transducer would be used to detect the formation of a crack on the hidden surface of the air separator or the progression of a crack under the surface of the air separator, while the eddy current sensor would be used for monitoring the formation of a crack on the surface of the air separator. However, it should be understood that any appropriate sensor depending upon the desired application could be used. In a preferred embodiment in which an eddy current sensor is used, it is more preferable to use the eddy current sensor described in U.S. Pat. No. 5,442,285. However, regardless of the type of sensor used it is preferable to utilize an appropriate support positioning device with the sensor to permit the sensor to be variably positioned over the surface to be monitored.

The holder assembly 101 comprises an axial member 104 as shown in FIG. 4. In a preferred embodiment, axial member 104 is an axial lead screw. A means for attaching the sensor 102a or 102b to the axial member 104 is shown as attachment apparatus 106. Preferably the attachment apparatus 106 will provide angular skew adjustments, for example by rotating the sensor in the cylindrical opening in holder 102b. It should be understood that adjustments to the angular position of an ultrasound transducer, for example, would permit optimization of defect detection. In a more preferable embodiment, the attachment apparatus 106 should be capable of interchangeably attaching either an eddy current sensor or ultrasound transducer to the axial member 104. For instance, the attachment apparatus 106 may include a specialized sensor holder such as eddy current probe holder 107b or an ultrasound transducer holder 107a as shown in FIG. 4. Alternatively, the attachment apparatus 106 could be configured to attach two or more sensors to the axial member 104 simultaneously.

An axial adjustment means 108 is preferably provided as shown in FIG. 4 to position the attachment apparatus 106 so that it can extend further into the access port. It should be understood that if an ultrasound transducer is provided, axial adjustments may also be used to determine the location of a defect from a time-of-flight table based on the distance of the transducer from the rotating member, the angle of the ultrasound transmission, and the return time of the ultrasound transmission.

The back end of the holder assembly 101 preferably provides a locking clamp mechanism 110. In a preferred embodiment the locking mechanism 110 provides three locking clamps, two of which are shown at 111a and 111b. The locking mechanism 110 holds the holder assembly 101 in place by clamping it to the sides of the access port 40 as shown in FIG. 3. In preferred embodiments, fine and coarse vertical adjustments 112 and 114, respectively, properly seat the sensor 102a or 102b for inspection.

If an ultrasound transducer is employed, a pumping system provides couplant to the ultrasound transducer. Couplant hoses 115 preferably run to each side of the holder assembly 101 and attach to injection ports 116 in the attachment apparatus 106. A gap is formed between the attachment apparatus 106 and the ultrasound transducer 102 which is defined as a couplant gap. The attachment apparatus 106 preferably provides a couplant gap adjustment 118 for allowing the ultrasound transducer to ride on top of the couplant resulting in better transmission of the ultrasound. The couplant hoses 115 and sensor cabling 122 exit the rear of the holder assembly 101 and are attached to a remote couplant pumping system and appropriate test instrumentation respectively. The appropriate test instrumentation would depend upon the particular sensor used in the nondestructive inspection device. For example, if an eddy current sensor is used, an eddy current test instrument would be provided. If an ultrasound transducer is used, a pulse echo ultrasonic device used for defect detection would be provided.

Referring back to FIG. 3, the inspection device 102 is inserted into the access hole 40 and clamped to the open diameter of the hole formed by access port 40. The sensor is positioned to the proper inspection location by adjusting the axial lead screw 104. FIG. 3 shows the inspection device locked in place. Once the inspection device is locked in place, the inspection begins by initiating the rotor by placing the combustion turbine rotor on turning gear. As the ultrasound transducer or eddy current sensor detects a flaw, the appropriate test instrument generates a signal clearly discernible by a trained nondestructive engineering (NDE) operator that can be compared to reference signals generated from artificial discontinuities in a calibration test block.

Figure 5:
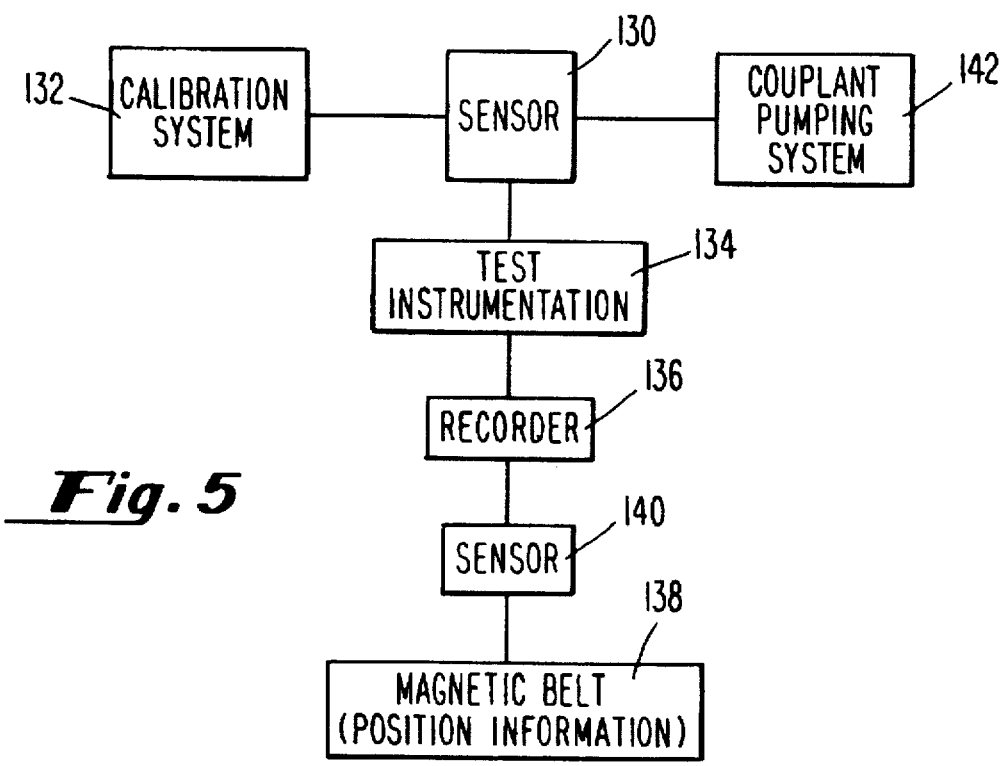
FIG. 5 is a block diagram of the inspection device according to a preferred implementation of the present invention.

A block diagram of a preferred implementation of the inspection device is shown in FIG. 5. Before actual inspection can take place, the sensor 130 is preferably calibrated against known defects in a section of the air separator known as a reference standard. A special calibration fixture and standard collectively shown as the calibration system 132 are preferably provided for this calibration. The calibration system 132 simulates the geometry of the actual field condition i.e., the formation of a crack in the air separator. The sensor 130 response from the artificial flaws is observed on a display of the test instrument 134 and the signal from the test instrument 134 is sent to a recorder 136 and used as the reference signal.

When the sensor 130 is an ultrasound transducer, the test instrument 134 is a pulse echo ultrasonic device having an A-scan display. Alternatively, when the sensor 130 is an eddy current sensor, the test instrument 134 is an eddy current defect detector having a polar and time base display. Both the pulse echo ultrasonic device and the eddy current defect detector are commercially available. Other variations and types of test equipment could likewise be used.

If a flaw is detected it is often important to know the angular position of the defect on or under the surface of the rotating member. Angular information preferably related to the air separator in a combustion turbine is obtained by placing a magnetic belt 138 around the combustion turbine shaft to monitor the magnetic belt's position as it rotates.

Preferably, Cermarium cobalt magnets are spaced apart approximately every 10 degrees and another eddy current sensor 140 is positioned to sense or count the magnets 141 as the shaft turns. The eddy current response is sent to a second channel of the recorder 136. The magnet position and ultrasound/eddy current flaw response can then be correlated to a known location on the air separator. It should be understood that encoders could be used on the shaft and decoders provided so that more accurate position information could be obtained.

The recorder 136 in one embodiment may be implemented using any suitable strip chart recorder. Alternatively, a data processor may be used to record and display the inspection data provided by the test instrumentation 134. However, it should be understood that numerous devices may be used to record the reference signal for subsequent use during actual inspection.

While the invention has been described and illustrated with reference to specific embodiments, those skilled in the art will recognize that modification and variations may be made without departing from the principles of the invention as described hereinabove and set forth in the following claims.

We claim:

1. A nondestructive inspection device, comprising;
   (a) an inspection sensor for detecting cracks in a rotating member of a turbine engine and for outputting a signal indicative of a crack, said rotating member having at least one cylindrical surface which rotates around a center axis of said rotating member;
   (b) a holder assembly capable of being coupled to said inspection sensor and for positioning said inspection sensor within said turbine engine adjacent said rotating member;
   (c) an angular position identification means being attached to one said cylindrical surface of said rotating member such that at least one a part of said angular position identification means rotates together with said rotating member, said angular position identification means being capable of generating a signal indicative of the angular position of said rotating member as said rotating member rotates; and
   (d) a recorder coupled to said inspection sensor and said angular position identification means for recording said signals output from said inspection sensor and from said angular position identification means so that the crack and a location of the crack can be ascertained.

2. The device of claim 1, wherein said inspection sensor is one of an ultrasound transducer and an eddy current sensor.

3. The device of claim 2, wherein said holder assembly is configured to position one of said ultrasound transducer and said eddy current sensor, and to provide skew adjustments for said one of said ultrasound transducer and said eddy current sensor.

4. The device of claim 1 wherein said rotating member is an air separator in a combustion turbine engine.

5. The device of claim 1, wherein said recorder is a strip chart recorder.

6. The device of claim 1, wherein said recorder is a data processor.

7. The device of claim 1, wherein said angular position identification means comprises:
   (a) a magnetic belt having a plurality of magnets, each magnet being individually identifiable, said magnetic belt being wrapped around said one cylindrical surface of said rotating member such that said magnetic belt rotates together with said rotating member; and
   (b) a second sensor for detecting each of said magnets as said magnetic belt rotates, said second sensor outputting a signal indicative of each magnet so detected.

8. The device of claim 7, wherein said second sensor is an eddy current sensor.

9. A nondestructive inspection device for inspecting a cylindrical surface of a rotating member in a turbine engine, comprising;
   (a) a sensor adapted for being disposed within a turbine engine adjacent said cylindrical surface of said rotating member, said sensor being one of an ultrasound transducer and an eddy current sensor, said sensor being capable of monitoring said rotating member for a crack therein; and
   (b) a holder assembly configured to position one of said ultrasound transducer and said eddy current sensor adjacent said cylindrical surface of said rotating member; and
   wherein said holder is capable of providing angular skew adjustments for rotating said one of said ultrasound transducer and said eddy current sensor to a predetermined angle for substantially optimal monitoring of said crack.

10. The device of claim 9, wherein said attachment apparatus comprises one of 1) an eddy current sensor holder, and 2) an ultrasound transducer holder, said eddy current sensor holder attaching said eddy current sensor to said axial member, said ultrasound transducer holder attaching said ultrasound transducer to said axial member.

11. The device of claim 9, wherein said axial member is a threaded lead screw.

12. The device of claim 9, further comprising:
   (a) an axial adjustment means connected to said axial member, said axial adjustment means being operable to adjust an extension of said axial member into said turbine.

13. The device of claim 9, wherein a gap is formed between said rotating member and said ultrasound transducer, said holder assembly comprising:
   (a) a couplant injection port receiving couplant from a couplant pumping system being remote from said nondestructive inspection device, said couplant so received filling said gap; and
   (b) a couplant gap adjustment means for adjusting said gap so that said ultrasound transducer rides on top of said couplant filling said couplant gap.

14. A method of detecting cracks in a rotating member while located in a turbine engine, comprising the steps of:
   (a) using one of an ultrasound transducer or an eddy current sensor to sense a characteristic of said rotating member while located within the turbine engine;
   (b) generating a signal indicative of said characteristic so sensed;

(c) recording a representation of said signal;

(d) comparing said representation to a known signal representation to identify said crack;

(e) monitoring the rotation of said rotating member;

(f) generating a signal indicative of said rotation so monitored; and (g) determining an angular position of said crack, if said crack is identified, based upon said signal indicative of said rotation so monitored.

15. The method of claim 14, further comprising the steps of:

(a) calibrating said inspection device using a reference standard having a known defect;

(b) generating from said calibration step said known signal representation; and (c) recording said known signal representation.

16. The method of claim 14, further comprising the steps of:

(a) positioning magnets around a surface of said rotating member so that said magnets rotate together with said rotating member, each magnet being separately identifiable;

(b) detecting each said magnet as said magnets rotate together with said rotating member;

(c) generating a signal indicative of an angular position of said rotating member based on said detection of said magnets; and (d) determining a location of said defective condition in said rotating member, if said defect has been identified, based on said signal indicative of the angular position of said rotating member.

* * * * *